United States Patent
Ono

(10) Patent No.: US 6,612,699 B2
(45) Date of Patent: Sep. 2, 2003

(54) OPHTHALMOLOGIC DIAGNOSTIC APPARATUS

(75) Inventor: Shigeaki Ono, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/183,714

(22) Filed: Jun. 27, 2002

(65) Prior Publication Data

US 2003/0016333 A1 Jan. 23, 2003

(30) Foreign Application Priority Data

Jun. 29, 2001 (JP) .......................... 2001-197949

(51) Int. Cl.[7] .................................. A61B 3/10

(52) U.S. Cl. ......................................... 351/221

(58) Field of Search ........................... 351/205, 206, 351/209, 210, 211, 221; 600/318, 320, 321, 504; 606/4

(56) References Cited

U.S. PATENT DOCUMENTS 5,594,512 A * 1/1997 Yoneda ...................... 351/206

FOREIGN PATENT DOCUMENTS

| JP | 2055031 | 2/1990 |
| JP | 9131320 | 5/1997 |

* cited by examiner

*Primary Examiner*—George Manuel
(74) *Attorney, Agent, or Firm*—Morgan & Finnegan, LLP

(57) ABSTRACT

There is provided an ophthalmologic apparatus. According to the ophthalmologic apparatus, irradiating times of tracking light and measuring light are measured for each measured part and then an energy integrated value Ex is calculated. Further, MPE is calculated based on a period from the time of irradiation to the current time and the proportion of the integrated value Ex to the MPE is calculated and displayed. When the proportion of the integrated value Ex to the MPE is 100% or more, tracking light irradiation is stopped. When the proportion of the integrated value Ex to the MPE has not reached 100%, measurement using the measuring light is conducted while the proportion of the integrated value Ex to the MPE is obtained.

7 Claims, 6 Drawing Sheets

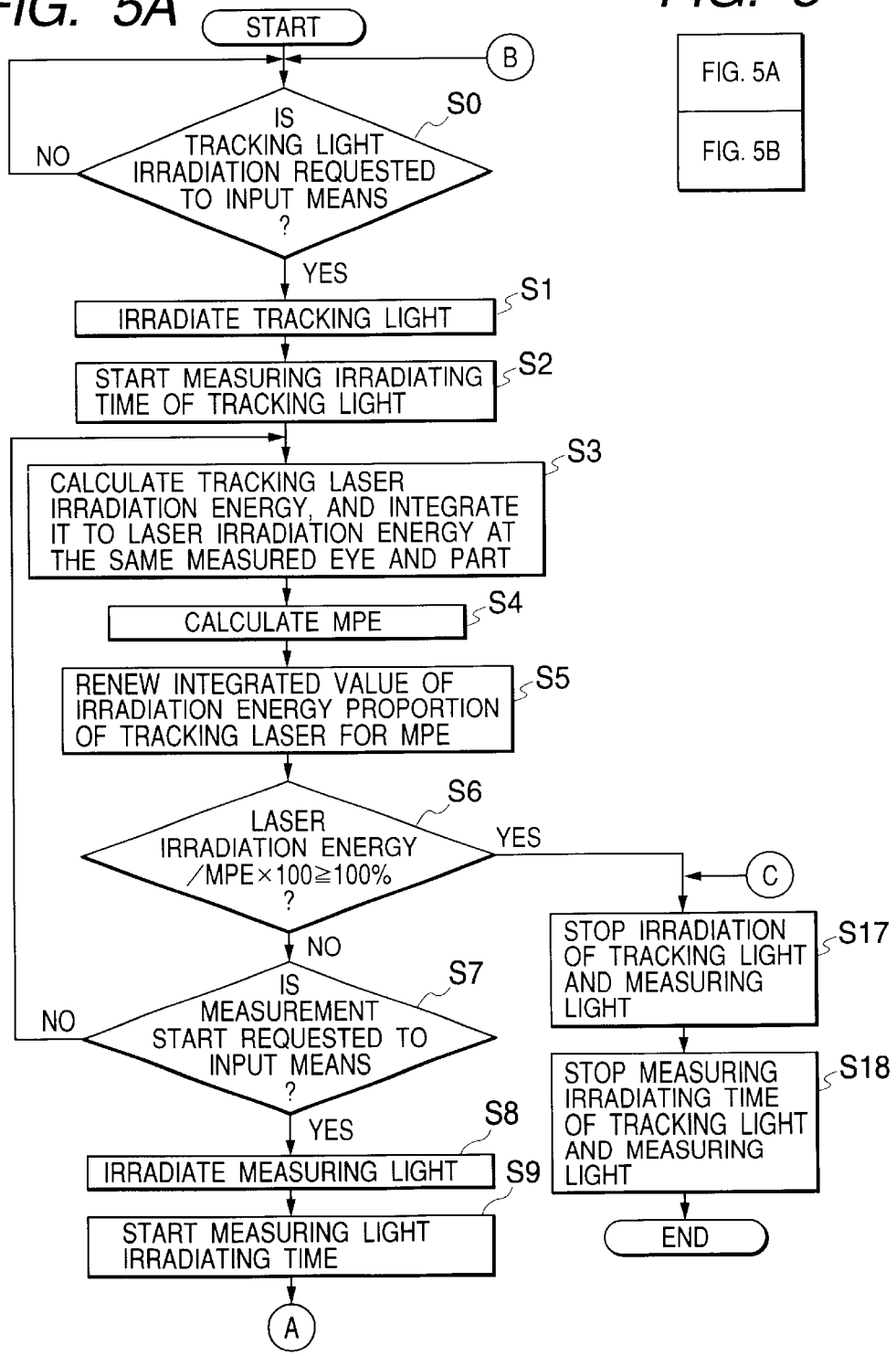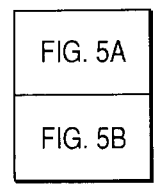

OPHTHALMOLOGIC DIAGNOSTIC APPARATUS

BACKGROUND OF THE INVENTION

1. Field of the Invention

The present invention relates to an ophthalmologic diagnostic apparatus for examining an eye fundus in an ophthalmologic office or the like.

2. Description of Related Art

An eye fundus blood flow meter, a laser flare cell meter, and the like have been known as ophthalmologic diagnostic apparatuses for irradiating laser light into an eye to measure a characteristic of an eye to be examined. The eye fundus blood flow meter is used to measure a blood flow of a blood vessel of an eye fundus which can be directly observed in a noninvasive manner. Various eye fundus blood flow meters for conducting laser light irradiation and utilizing a Doppler measurement theory or a speckle phenomenon have been devised, which are now being anticipated for use for a wide range of applications.

In the ophthalmologic diagnostic apparatus as described above, for the safety of an eye of a person to be examined, a maximum permissible exposure (MPE) has been defined by American National Standards Institute (ANSI) as the maximum permissible laser energy of laser light which may be irradiated.

In the conventional ophthalmologic diagnostic apparatus as described above, an operator himself measures an irradiation time of measurement laser light to an eye fundus to perform irradiation operation such that irradiation energy does not exceed the MPE, thus causing an inconvenience to the operator.

In order to solve such a problem, an apparatus for conducting time integration of outputs of measurement laser light for each person to be examined and calculating irradiation energy to display a message, to give an alarm, to stop laser light irradiation, or the like so that irradiation energy of the measurement laser light does not exceed the MPE is proposed in Japanese Patent Application Laid-Open No. 9-131320.

Also, an apparatus for detecting the amount of light illuminated to an eye of a person, integrating it, comparing the integrated amount of light with the safety permissible cumulative amount of light that may be illuminated to an eye of a person, and controlling the amount of light to be illuminated in order to protect an eye of a person when the integrated amount of light exceeds the safety permissible cumulative amount of light is proposed in Japanese Patent No. 2685239. According to this invention, the safety permissible cumulative amount of light that may be illuminated to an eye of a person are controlled for each of left and right eyes.

However, in an apparatus for irradiating laser light to an eye to be examined, such as the eye fundus blood flow meter, irradiation light is irradiated not over the entire eye fundus but per each predetermined area. In view of this, it is desirable that laser irradiation energies are controlled for each of left and right eyes to be examined and for each measurement position.

When the laser irradiation energies are calculated for each person to be examined and for each of left and right eyes so that they do not exceed the MPE as in the above conventional example, there is a case where the number of measurements that may be actually performed is limited for the safety of a person to be examined, when using an apparatus for irradiating laser illumination light to a local region such as a blood vessel of an eye to be examined, such as the eye fundus blood flow meter, to conduct a measurement.

SUMMARY OF THE INVENTION

The present invention has been devised to provide improvements over the above-mentioned conventional art. Specifically, an object of the invention is to provide an ophthalmologic apparatus in which the number of measuring light irradiation can be increased while securing the safety of a person to be examined.

In order to achieve the above-mentioned object, there is provided an ophthalmologic apparatus comprising an irradiation optical system for irradiating a light beam to an eye to be examined, a timer for measuring an irradiating time of the light beam; and a controller which controls the irradiating time, by calculating integrated irradiation energy for each of a plurality of positions on the eye to be examined based on the irradiating time measured by the timer.

Further, according to the present invention, the ophthalmologic apparatus may further comprise a sensor for monitoring the light beam output, and the controller calculates the integrated irradiation energy based on an output of the sensor and the irradiating time measured by the timer.

Further, according to the present invention, the apparatus may further comprise means for discriminating between left and right eyes to be examined, and the controller controls the position based on a result of the above discrimination.

Further, according to the present invention, the apparatus may further include means for detecting an irradiation position of a light beam to an eye fundus and the controller can specify the above-mentioned position based on the discrimination between the left and right eyes and the inputted irradiation position.

Further, according to the present invention, the controller can set a predetermined region as the above-mentioned position and control the sum of irradiation energies by corresponding to measurement positions present in the region in correspondence with the position.

Further, according to the present invention, the apparatus may further comprise a display unit for displaying the integrated irradiation energy at each of the above-mentioned positions. The display unit may further display the proportion of the integrated irradiation energy to a predetermined value.

Further, the present invention may be constructed such that when a value of the integrated irradiation energy exceeds a predetermined value or larger, an alarm is given or irradiation of the light beam is restricted.

DESCRIPTION OF THE PREFERRED EMBODIMENTS

The present invention will be described in detail based on embodiments of the invention as indicated below.

Figure 1:
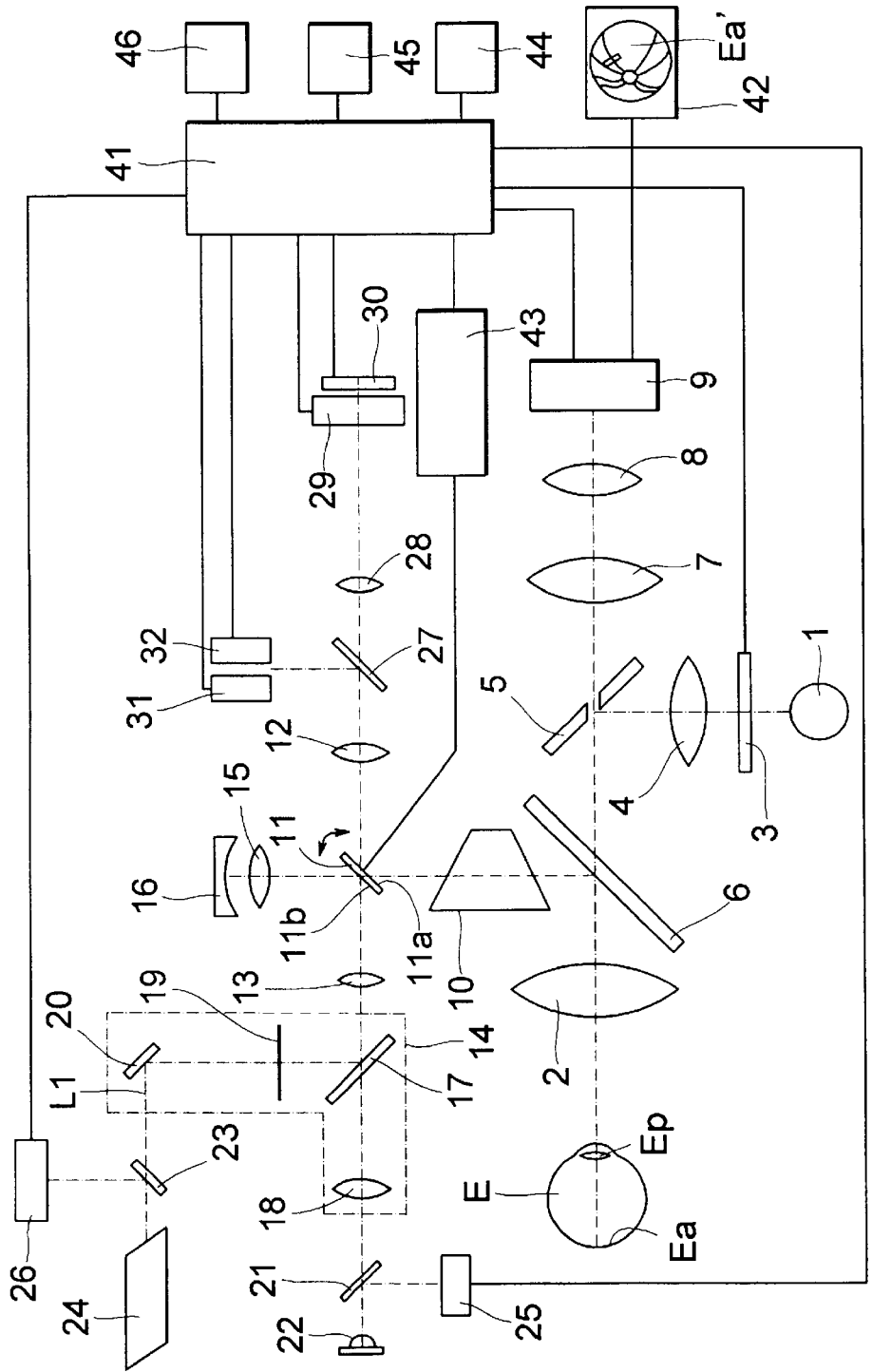
FIG. 1 is a configuration diagram showing an embodiment of the present invention.

FIG. 1 is a configuration diagram showing an embodiment of the present invention in which the present invention is applied to an eye fundus blood flow meter. On an illumination optical path extending from an observation light source 1 composed of a tungsten lamp or the like for emitting white light, to an objective lens 2 opposing an eye E to be examined, a transmission type liquid crystal plate 3, a relay lens 4, a mirror 5 having an aperture, and a band-pass mirror 6 are disposed in the stated order so as to compose an illumination optical system. The transmission type liquid crystal plate 3 is a fixed index display element movable along the optical path and located in a position substantially optically conjugated with an eye fundus Ea of the eye E to be examined. The band-pass mirror 6 transmits light having a wavelength of a yellow band and reflects almost all the light fluxes other than such light. An eye fundus observation optical system is located in the rear side of the mirror 5 having an aperture, which is composed of a focusing lens 7 movable along the optical path, an imaging lens 8, and a two-dimensional CCD camera 9 that are disposed in order.

On an optical path along a reflecting direction of the band-pass mirror 6, an image rotator 10 and a galvanometric mirror 11 which has a rotation axis perpendicular to a paper surface and whose both surfaces are polished are located. A relay lens 12 movable along the optical path is located in a reflecting direction of a lower side reflective surface 11a of the galvanometric mirror 11 and a lens 13 is located in a reflecting direction of an upper side reflective surface 11b thereof. Further, a focus unit 14 integrally movable along the optical path of the lens 13 is arranged. Note that the galvanometric mirror 11 has a notch portion located under the above rotation axis. In addition, a front-side focal plane of the lens 13 is conjugated with the pupil of the eye E to be examined and the galvanometric mirror 11 is located on the focal plane. Further, a lens 15 and a concave mirror 16 are disposed in the rear of the galvanometric mirror 11 to constitute a relay optical system for guiding, to the upper side reflective surface 11b of the galvanometric mirror 11, a light flux passing through the notch portion without being reflected by the lower side reflective surface 11a of the galvanometric mirror 11.

In the focus unit 14, a dichroic mirror 17 and a lens 18 are disposed on the same optical path as the lens 13. In addition, a mask plate 19 having a rectangular diaphragm and a mirror 20 are disposed on the optical path of a reflecting direction of the dichroic mirror 17.

Also, a half mirror 21 and a measuring light source 22 such as a laser diode for emitting collimated coherent light (for example, collimated coherent red light) are disposed on the optical path of the light incidence direction of the lens 18. Further, a half mirror 23 and a tracking light source 24 such as a helium neon laser for emitting, for example, green light, which allows high luminance and is different from other light sources are disposed on the optical path of the light incidence direction of the mirror 20. A photosensor 25 is located in a reflecting direction of the half mirror 21 and a photosensor 26 is located in a reflecting direction of the half mirror 23.

On the optical path of the reflecting direction of the lower side reflective surface 11a of the galvanometric mirror 11, a relay lens 12 movable along the optical path, a dichroic mirror 27, a magnifying lens 28, an image intensifier 29, and a one-dimensional CCD 30 are disposed in the stated order so as to constitute a blood vessel detection system. In addition, photomultipliers 31 and 32 are disposed in a reflecting direction of the dichroic mirror 27 to compose a measuring light receiving optical system. Note that all the optical paths are indicated on the same plane in the drawing for convenience of the description. However, for example, the reflecting direction of the dichroic mirror 27 is perpendicular to a paper surface.

Also, the transmission type liquid crystal plate 3, the focusing lens 7, the focus unit 14, and the relay lens 12 as described above are moved in an optical axis direction in conjunction with operating a focusing knob (not shown). Thus, the eye fundus Ea, the transmission type liquid crystal plate 3, the eye fundus of an operator's eye "e", the mask plate 19, and the light receiving surface of the image intensifier 29 are always optically conjugate with each other.

Respective output terminals of the two-dimensional CCD camera 9, the photosensors 25 and 26, the image intensifier 29, the one-dimensional CCD 30, and photomultipliers 31 and 32 are connected with a system controller 41. In addition, another output terminal of the two-dimensional CCD camera 9 is connected with a first display device 42 such as a television monitor. Output terminals of the system controller 41 are connected with the transmission type liquid crystal plate 3 and a galvanometric mirror control circuit 43 for operating the galvanometric mirror 11. Further, the system controller 41 is connected with an input device 44, a second display device 45 such as a television monitor, and a detector 46 for detecting left and right eyes.

Here, a state in which lights emitted from the respective light sources are led to the eye E to be examined and the reflected and scattered lights are led to the operator's eye "e" or the light receiving surfaces of the photomultipliers 31 and 32 and the image intensifier 29 will be described. White light emitted from the observation light source 1 illuminates the transmission type liquid crystal plate 3 from behind, is passed through the relay lens 4, and reflected by the mirror 5 having an aperture. Of the reflected white light, only the light having a wavelength of a yellow band is transmitted through the band-pass mirror 6, passed through the objective lens 2, and then temporarily imaged on a pupil Ep of the eye E to be examined as an eye fundus illumination light flux image "I". Then, substantially uniform illumination is conducted for the eye fundus Ea. At this time, a fixed index F (not shown) is displayed on the transmission type liquid crystal plate 3. The fixed index is projected to the eye fundus Ea by illumination light and presented to the eye E to be examined as an index image F'.

Figure 2:
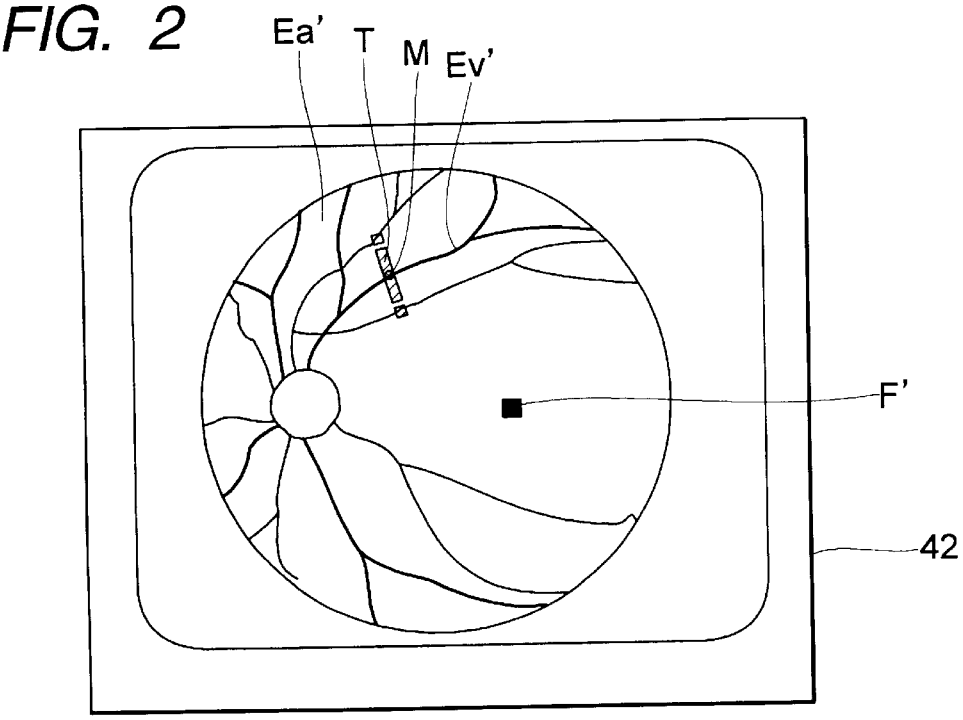
FIG. 2 is an explanatory view of an observation eye fundus image after the completion of focusing.

The reflected light from the eye fundus Ea is returned through the same path, picked up as an eye fundus observation light flux "O" from the pupil, passed through an opening provided at the center of the mirror 5 and the focusing lens 7, and enters into the two-dimensional CCD camera 9 through the imaging lens 8. Thus, an eye fundus image Ea' is displayed on the first display device 42 and becomes observable by the operator. While the eye fundus image Ea' is observed, an alignment of an apparatus is performed. FIG. 2 shows the eye fundus image Ea' displayed on the first display device 42 when the eye fundus Ea of the eye E to be examined is observed by the operator.

Measuring light as a collimated light beam which is emitted from the measuring light source 22 is passed through the half mirror 21 and the lens 18 and transmitted through the dichroic mirror 17. In addition, tracking light as a light beam which is emitted from the tracking light source 24 is passed through the half mirror 23 and reflected by the mirror 20. Then, the reflected tracking light is shaped in a predetermined form by the mask plate 19 having the rectangular diaphragm and reflected by the dichroic mirror 17, thereby being overlapped with the above-described measuring light.

At this time, the measuring light is imaged in a spot form by the lens 18 in a position conjugate with the center of opening of the mask plate 19. Further, the measuring light and the tracking light are passed through the lens 13 and are reflected by the upper side reflective surface 11b of the galvanometric mirror 11. The reflected lights are passed through the lens 15, and then reflected by the concave mirror 16, to thus pass through the lens 15 again, thereby being returned toward the galvanometric mirror 11. Here, the galvanometric mirror 11 is located in a position conjugate with the pupil of the eye to be examined. In addition, the concave mirror 16 and the lens 15 are concentrically disposed on the optical axis and they are provided with a relay system function for imaging light on the galvanometric mirror 11 at a magnification of −1, in cooperation with each other.

Therefore, the light fluxes reflected by the upper side reflective surface 11b of the galvanometric mirror 11 is returned to the notch portion of the galvanometric mirror 11 and then travels toward the image rotator 10 without being reflected thereby. Both light fluxes deflected toward the objective lens 2 by the band-pass mirror 6 after passing through the image rotator 10 are irradiated to the eye fundus Ea through the objective lens 2.

Figure 3:
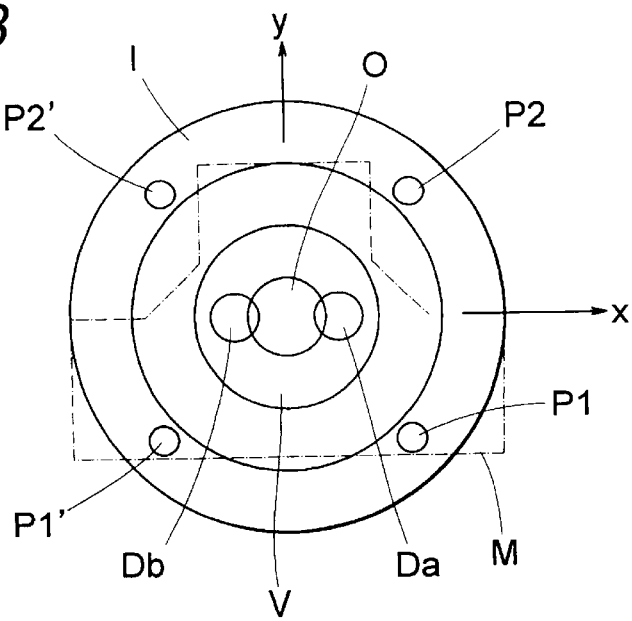
FIG. 3 is an explanatory view of an arrangement of light fluxes on a pupil.

Thus, the measuring light and the tracking light are reflected by the upper side reflective surface 11b of the galvanometric mirror 11 and made incident on the galvanometric mirror 11 with a state in which lights to be returned again are decentered from the optical axis of the objective lens 2. As shown in FIG. 3, the lights are imaged on the pupil Ep as a spot image P2 or P2' and then irradiated to the eye fundus Ea in a punctiform fashion.

The scattered and reflected lights of the measuring light and the tracking irradiation light from the eye fundus Ea are condensed again by the objective lens 2. Most of the light fluxes are reflected by the band-pass mirror 6, passed through the image rotator, and reflected by the lower side reflective surface 11a of the galvanometric mirror 11. Then, the reflected lights are passed through the relay lens 12 and separated into the measuring light and the tracking light by the dichroic mirror 27.

The tracking light is transmitted through the dichroic mirror 27 and imaged on the photoelectric surface of the image intensifier 29 as a blood vessel image Ev' magnified by the magnifying lens 28 as compared with the eye fundus image Ea' obtained by the eye fundus observation optical system. The image is amplified and then picked up on the one-dimensional CCD 30. Then, data indicating the amount of shifts of the blood vessel image Ev' is produced by the system controller 41 based on the blood vessel image Ev' picked up by the one-dimensional CCD 30. The blood vessel image Ev and the amount of shifts are outputted to the galvanometric mirror control circuit 43. The galvanometric mirror control circuit 43 operates the galvanometric mirror 11 so as to compensate for the amount of shifts. Thus, tracking of a blood vessel in a region to be measured is conducted.

Also, the measuring light is reflected by the dichroic mirror 27 and is received by the photomultipliers 31 and 32. The respective outputs of the photomultipliers 31 and 32 are inputted to the system controller 41. A frequency analysis is conducted for such receiving signals as in a conventional example to obtain a blood flow rate of the eye fundus Ea.

The scattered and reflected lights of the measuring light and the tracking irradiation light from the eye fundus Ea are condensed again by the objective lens 2. A part of these light fluxes which is transmitted through the band-pass mirror 6 travels the same optical path as the reflected and scattered light of the light flux emitted from the observation light source 1, from the eye fundus Ea of the eye E to be examined and reaches the two-dimensional CCD 9.

The output signal of the two-dimensional CCD 9 is inputted to the system controller 41, converted into a digital signal by an A/D converter (not shown). Thus, an eye fundus image is stored in response to each eye fundus image storage request from the input device 44 or for each measurement.

Further, the output signal of the two-dimensional CCD 9 is inputted to the first display device 42. Thus, as shown in FIG. 2, a tracking index image T and a measuring light image M can be observed together with the observation eye fundus image Ea' by the operator.

Also, a part of collimated measuring light emitted from the measuring light source 22 is reflected by the half mirror 21 and received by the photosensor 25. The output of the photosensor 25 is inputted to the system controller 41 to monitor the output of the measuring light source 22. This output is used for calculating irradiation energy of the measuring light source 22. Similarly, a part of tracking light emitted from the tracking light source 24 is reflected by the half mirror 23 and received by the photosensor 26. The output of the photosensor 26 is inputted to the system controller 41 to monitor the output of the tracking light source 24. This output is used for calculating irradiation energy of the tracking light source 24.

Figure 4:
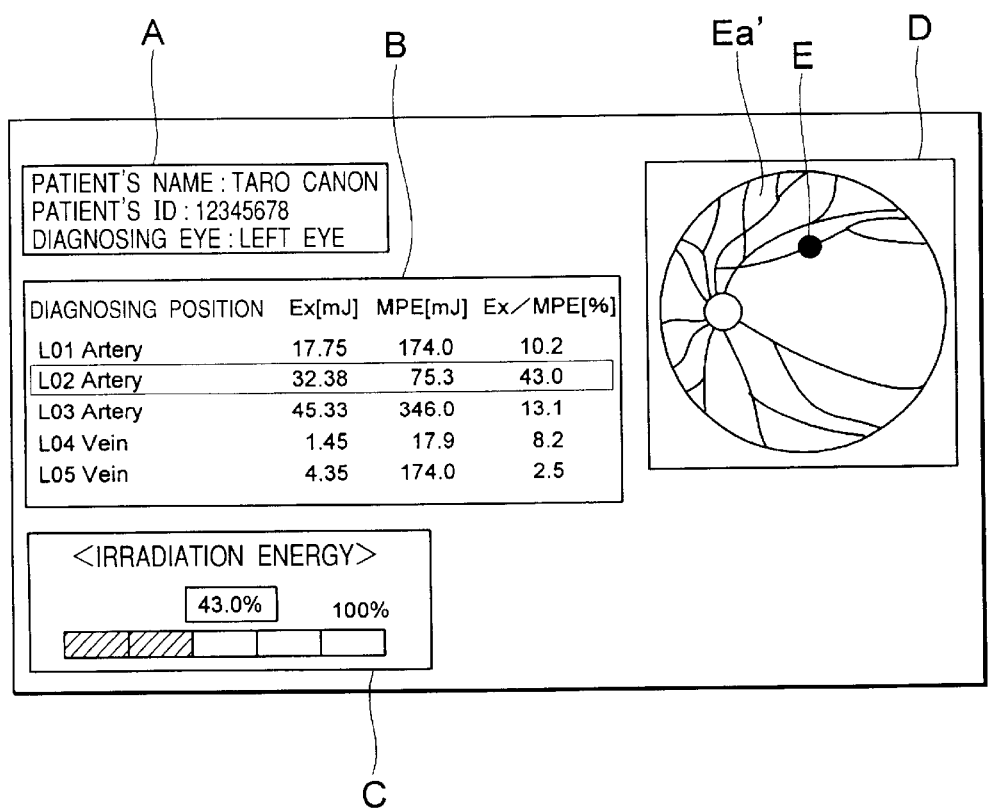
FIG. 4 is a front view indicating an display example of a second display device.

Next, a concrete operation example will be described. First, an operator selects a diagnosing position of a blood vessel to be measured and inputs it from the input device 44. FIG. 4 shows display contents of the second display device 45. In FIG. 4, a patient's name, a patient's ID, and information of a diagnosing eye are displayed on an area A. The information of the diagnosing eye includes information of left and right eyes which is inputted from the input device 44 or information of left and right eyes which is detected by the detector 46. Note that the patient's name and the patient's ID can be selected and inputted from the input device 44. Diagnosing positions are displayed on an area B. An integrated value Ex of laser irradiation energy for each position, maximum permissible laser energy MPE, and the proportion of the integrated value Ex to the MPE are displayed adjacent to the diagnosing positions.

Note that the diagnosing position can be selected or newly registered by the input device 44. The proportion of the integrated value Ex of laser irradiation energy to the MPE at the selected diagnosing position is displayed on an area C by using a numeric value and a bar. An eye fundus image Ea' specified by the patient's name, the patient's ID, and the diagnosing eye which are displayed on the area A is displayed on an area D. A position on the eye fundus Ea corresponding to the diagnosing position selected in the area B is indicated by reference symbol E.

According to this embodiment, "L02Artery" is selected as the diagnosing position. With respect to this diagnosing position, it is indicated that the integrated value Ex of laser irradiation energy is 32.38 mJ, the MPE is 75.3 mJ, and the proportion of the integrated value Ex of laser irradiation energy to the MPE is 43.0%.

An operator operates a joystick (not shown) and conducts an alignment so as to align the optical axis of the objective lens 2 with that of the eye E to be examined. Next, while observing the eye fundus image Ea' on the first display device 42, the operator operates the above focus knob to focus on the eye fundus Ea of the eye E to be examined. Thus, as described above, the fixed index F on the transmission type liquid crystal plate 3 and the eye fundus Ea become optically conjugate with each other so that it is presented to the eye E to be examined. Then, in order to locate a part to be examined near a substantially central region of an observation view field, the operator operates the input device 44 to shift the fixed index F so that the eye E to be examined is led thereto.

Figure 5B:
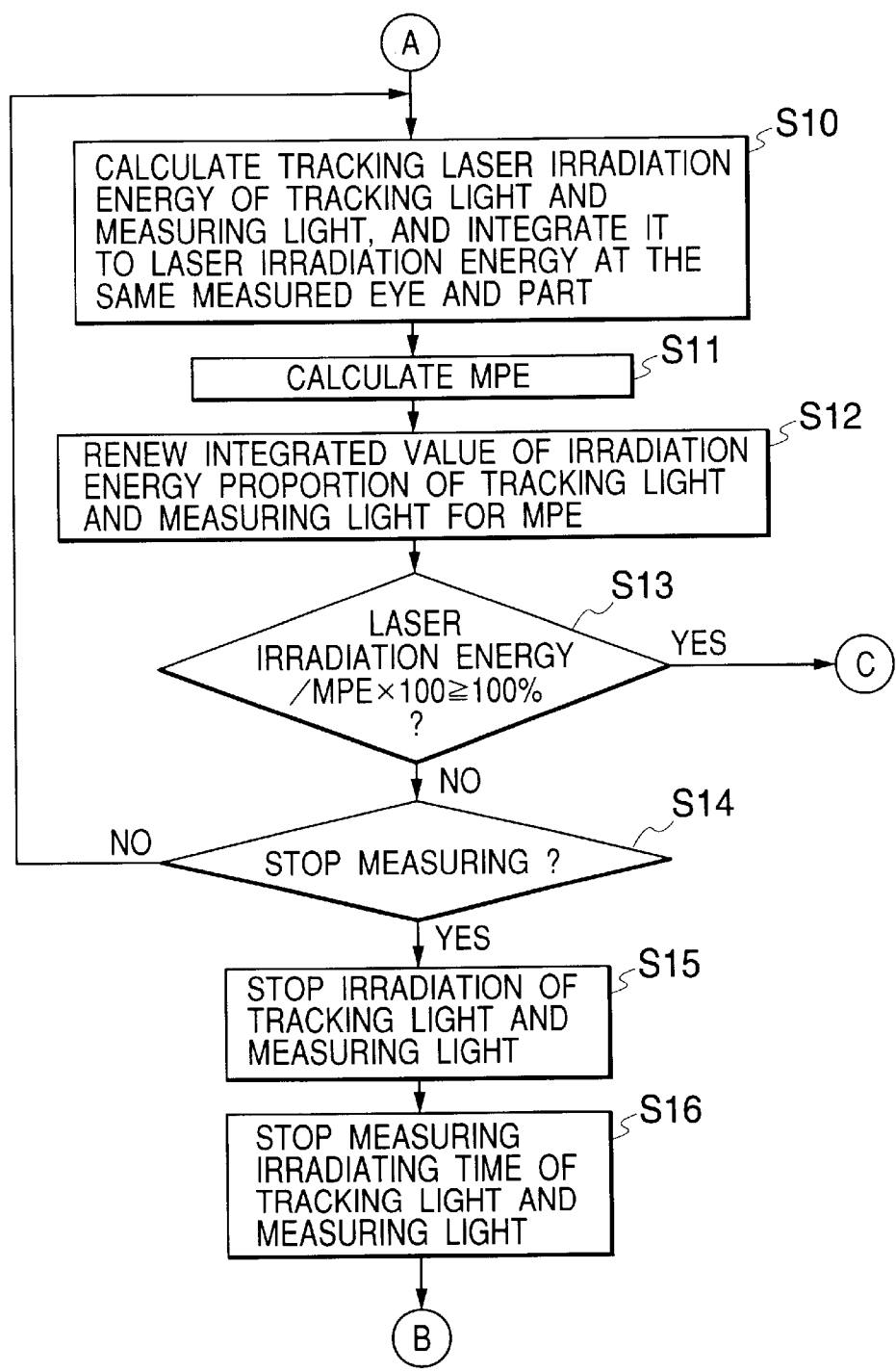
FIG. 5 is comprised of FIGS. 5A and 5B showing flow charts of an operation.

FIGS. 5A and 5B are flow charts indicating an operation of the system controller 41. When a request for irradiating tracking light to the eye fundus Ea is inputted by operating the input device 44, the system controller 41 determines that tracking light irradiation is requested to the input device 44 in step SO. When the tracking light is irradiated in step S1, the tracking index image T is projected to the eye fundus of the eye E to be examined. In synchronization with this, measurement of an irradiating time of the tracking light by a timer provided in the system controller 41 is started in step S2.

Further, in step S3, irradiation energy Ex' of the tracking laser light for the current measurement at the selected diagnosing position E is calculated. The energy Ex' is calculated by the following equation, $$Ex' = Ptrk * Ttrk / 1000 \; [mJ]$$

where Ttrk indicates an irradiating time of the tracking light and Ptrk indicates a value obtained by converting the output of the tracking light source 24 which is outputted from the photosensor 26 into the amount of light emitted to an object.

Further, the energy Ex' is added to the integrated value Ex of laser irradiation energy up to the preceding measurement. Thus, the integrated value Ex of laser light irradiation energy including the integrated value obtained by the current measurement is calculated. In step S4, the MPE for the selected diagnosing position is calculated using, as a parameter, a period from the time when the laser light is irradiated for the first time at the selected diagnosing position to the current time.

Note that, in this embodiment, a helium neon laser having a wavelength of 543 nm and an output of 4 mW is used as the tracking light source 24 and a semiconductor laser light source having a wavelength of 675 nm and an output of 200 $\mu$W is used as the measuring light source 22.

However, if, at the current time, 24 hours or more have elapsed from the time of final laser irradiation, the integrated value Ex of laser irradiation energy is reset.

In step S5, a percentage of the proportion of the integrated value Ex to the MPE is calculated and the numeric value and the bar which are displayed on the area C of the second display device 45 are renewed. When the proportion of the integrated value Ex to the MPE is 100% or more in step S6, the tracking light irradiation is stopped in step S17 and the measurement of the irradiating time of the tracking light by the timer is stopped in step S18. Thus, the measuring sequence is completed. At this time, the region indicating "100%" of the bar displayed on the area C shown in FIG. 4 is blinked for error indication. Further, a buzzer is sounded to give an alarm.

When the proportion of the integrated value Ex to the MPE does not reach 100% in step S6, the control is transferred to step S7 and a request for a start of measurement from the input device is waited for. When the request for the start of measurement from the input device is not detected in step S7, the control is returned to step S3 and an operation from step S3 to step S7 is repeated.

At this time, the operator operates the input device 44 to drive the image rotator 10 such that the tracking index image T is perpendicular to the blood vessel Ev to be measured. Further, an angle of the galvanometric mirror 11 is controlled such that measuring light M is irradiated onto the blood vessel Ev to be measured.

After the preparations for the measurement are thus completed, the tracking start request is inputted from the input device 44. The system controller 41 calculates the amount of shift between the blood vessel Ev to be measured and the tracking central position, based on the blood vessel image picked up by the one-dimensional CCD 30. Then, in order to correct the amount of shift, the system controller 41 controls the galvanometric mirror 11 through the galvanometric mirror control circuit 43. Thus, the tracking operation for the blood vessel Ev to be measured is started.

After the tracking operation becomes stable, when the measurement start request is inputted from the input device 44, the system controller 41 determines that the measurement start is requested to the input device 44 in step S7. Thus, in step S8, the measuring light is irradiated to the blood vessel to be measured. In synchronization to this, measurement of an irradiating time of the measuring light by the timer provided in the system controller 41 is started in step S9.

In step S10, laser irradiation energy Ex' for the current measurement at the selected diagnosing position is calculated. The laser irradiation energy Ex' is calculated by the following equation, $$Ex' = (Ptrk * Ttrk + Pmes * Tmes) / 1000 \; [mJ]$$

where Ttrk indicates an irradiating time of the tracking light, Tmes indicates an irradiating time of the measuring light, Ptrk indicates a value obtained by converting the output of the tracking light source 24 which is outputted from the photosensor 26 into the amount of light emitted to an object, and Pmes indicates a value obtained by converting the output of the measuring light source 22 which is outputted from the photosensor 25 into the amount of light emitted to an object.

Further, the laser irradiation energy Ex' is added to the integrated value Ex of laser irradiation energy up to the preceding measurement. Thus, the integrated value Ex of laser irradiation energy at the selected diagnosing position, which includes the value obtained by the current measurement, is calculated.

Further, in step S11, the MPE for the selected diagnosing position is calculated. In step S12, a percentage of the proportion of the integrated value Ex of laser irradiation energy to the MPE at the selected diagnosing position is calculated and the numeric value and the bar which are displayed on the area C of the second display device 45 are renewed.

When the proportion of the integrated value Ex of laser irradiation energy to the MPE is 100% or more in step S13, the tracking light irradiation is stopped in step S17 and the measurement of the irradiating time of the tracking light by the timer is stopped in step S18. Thus, the measuring sequence is completed. At this time, the region indicating "100%" of the bar displayed on the area C shown in FIG. 4 is blinked for error indication. Further, a buzzer is sounded to give an alarm. Next measurement at this diagnosing position cannot be conducted until the MPE is reset.

When the proportion of the integrated value Ex of laser irradiation energy to the MPE does not reach 100% in step S13, the control is transferred to step S14 and the completion of measurement data collection is waited. When the collecting of measurement data is not completed, the control is returned to step S10 and an operation from step S10 to step S14 is repeated.

When the completion of measurement data collection is detected in step S14, the irradiation of the tracking light and the measuring light is stopped in step S15 and the measurement of the irradiation times of the tracking light and the measuring light is stopped in step S16. Then, the control is returned to step S0 and the similar operation is repeated. At this time, the final proportion of the integrated value Ex of laser irradiation energy to the MPE is stored into a memory and used at next measurement.

Also, the system controller 41 stores a position of the fixed index F on the transmission type liquid crystal plate 3, an angle of the galvanometric mirror 11, and an angle of the image rotator 10. These stored values are reflected on the position E indicating the diagnosing position on the eye fundus image displayed on the area D shown in FIG. 4. In addition to this, the stored values are used to perform control for irradiating the tracking light and the measuring light to the same positions as the preceding measurement when next measurement is conducted at the same diagnosing position.

Note that, according to this embodiment, the tracking laser light output and the measuring laser light output are monitored by the photosensors 25 and 26. However, according to another embodiment, when variations in the outputs of the tracking laser light and the measuring laser light are small, predetermined values may be used as the outputs for the calculation of irradiation energy.

Next, another concrete example will be described. In actual measurement, when tracking laser light and measuring laser light are irradiated to a diagnosing position, there is a case where the eye to be examined moves or the first irradiation position is shifted from the actual diagnosing position. In such a case, a region to which the tracking light and the measuring light are actually irradiated becomes wider than that corresponding to the diagnosing position.

According to this concrete example, a large number of diagnosing positions are present on the eye fundus Ea of the eye E to be examined. Thus, when the diagnosing position at which the measurement has been conducted at least one time is present near a diagnosing position for which the proportion of the integrated value Ex of laser irradiation energy to the MPE is to be calculated, the laser irradiation energy value at such a diagnosing position is also integrated.

Figure 6:
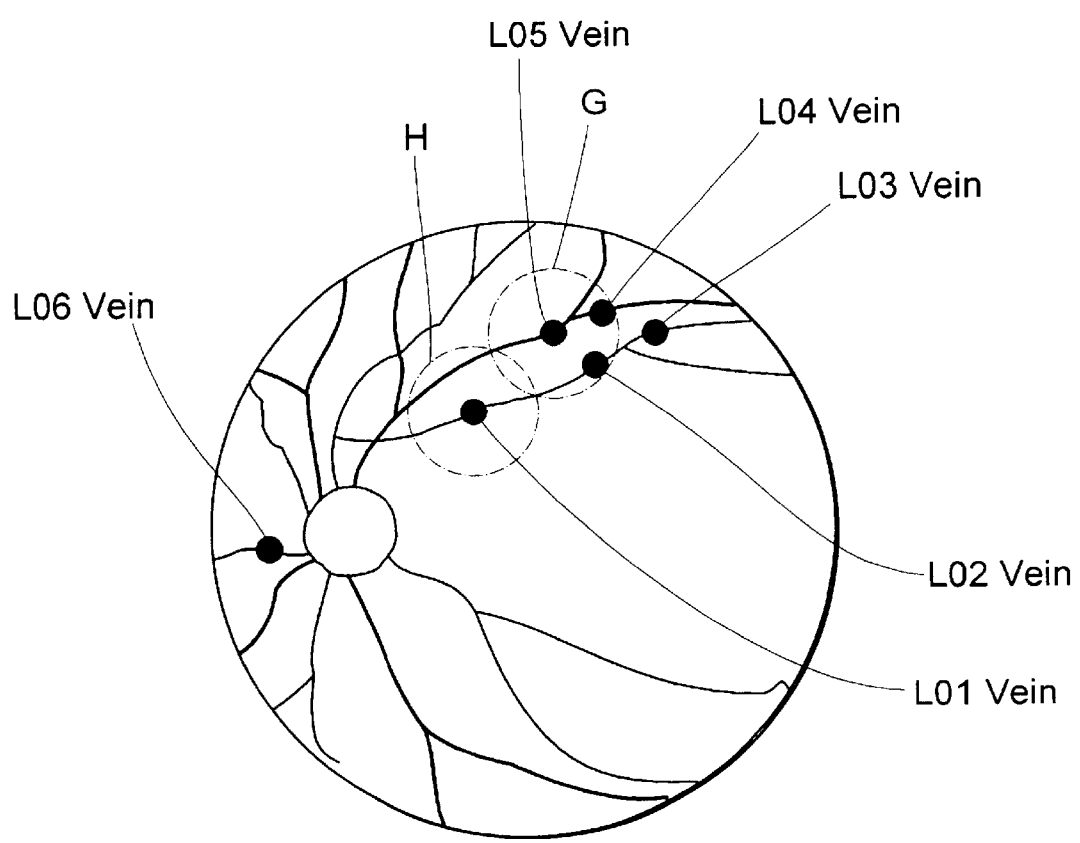
FIG. 6 is an explanatory view of an operation according to another embodiment.

FIG. 6 is a view in which diagnosing positions are plotted on the eye fundus image. When a series of measurement operations is conducted, the system controller 41 is operated as indicated by the flow charts shown in FIGS. 5A and 5B. However, the difference in this example resides in a method of calculating laser irradiation energies Ex' of the tracking light and the measuring light in steps S3 and S10, in that the same measured eye and part are divided into regions such as a region G and a region H in obtaining an integrated value of laser irradiation energies.

According to this concrete example, the case where the proportion of the laser irradiation energy to the MPE (hereinafter referred to as "Ex/MPE") at the diagnosing position L05Vein is calculated by the system controller 41 is indicated. In FIG. 6, a region G is a region having about 1.5 papilla diameter with the diagnosing position L05Vein at its center. This region is set as a region for calculating the laser irradiation energy at the diagnosing position L05vein.

In steps S3 and S10, laser irradiation energies Ex' at the respective registered measurement parts which are located within the region G are calculated and summed. The laser irradiation energy Ex'(g) in the region G is given by the following equation. Here, when the values displayed on the area B shown in FIG. 4 are used, the following value is obtained as the laser irradiation energy. That is, $$Ex'(g) = Ex'(L05) + Ex'(L02) + Ex'(L04)$$
$$= 4.35 + 32.38 + 1.47 = 38.2 \text{ [mJ]}.$$

Further, in steps S4 and S11, the MPE in the region G is calculated based on the time when the tracking laser light or the measuring laser light is irradiated to the region G for the first time. In steps S5 and S12, Ex(g)/MPE is calculated. Here, when the values displayed on the area B shown in FIG. 4 are used, the proportion of the laser irradiation energy to the MPE (Ex'(g)/MPE) at L05Vein is obtained by the following equation, $$Ex'(g)/MPE = 38.2/174.0 = 22.95[\%]$$

Further, in steps S5 and S 12, the value of Ex'(g)/MPE is displayed on the second display device 45 as the proportion of the laser irradiation energy to the MPE at the diagnosing position L05Vein.

Particularly, the safety is an important consideration when using laser light. Thus, the example of the ophthalmologic apparatus using the laser light is indicated in this embodiment. However, the similar operation can be implemented also with respect to general incoherent light other than the laser light. In addition, the eye fundus blood flow meter having a specific effect is described as the embodiment of the invention. However, the present invention is not limited to such an apparatus and can be applied to, for example, an eye treatment apparatus for conducting eye treatment by laser light irradiation.

Thus, according to the embodiment, the following effects are obtained.

(1) Time integration of measuring light outputs is conducted for each of left and right eyes to be examined and for each diagnosing position to calculate irradiation energy and MPE. Thus, while securing the safety of a person to be examined, measuring light irradiation can be easily conducted with reliability so as not to exceed the MPE, without reducing the number of measurements that may be actually performed.

(2) The means for inputting information of left and right eyes to be examined is provided. Thus, the left and light eyes to be examined can be specified with high reliability.

(3) The means for inputting an irradiation position of measuring light to an eye fundus is provided. Thus, the irradiation position of the measuring light to the eye to be examined can be specified with high reliability.

(4) The means for detecting the left and light eyes to be examined is provided. Thus, the left and light eyes to be examined can be specified with high reliability without troublesome operations by an operator.

(5) The means for detecting an irradiation position of measuring light to the eye fundus is provided. Thus, the irradiation position of the measuring light to the eye to be examined can be specified with high reliability without troublesome operations by an operator.

(6) A predetermined region including the diagnosing position of the eye fundus at its center is set as the irradiation position of the measuring light to the eye fundus and all of the irradiation energies at the diagnosing positions present within the region are integrated. Further, the MPE in the region is calculated. Thus, the irradiation energy of the measuring light irradiated to the vicinity of the diagnosing position when the eye to be examined has moved or when the alignment is conducted can be taken into account and the safety of a person to be examined can be obtained with higher reliability.

(7) The output measuring means for measuring a measuring light output is provided. Thus, even when the output is changed or a laser output is varied, the irradiation energy can be accurately calculated.

(8) The display device for displaying irradiation energy information is provided. Thus, an operator can be easily informed of the irradiation energy, thus contributing to securing of the safety of a person to be examined.

(9) The ratio between an irradiation value and a predetermined value is displayed on the display device. Thus, the irradiation energy can be grasped more easily.

(10) When the irradiation energy exceeds a predetermined value, a message is displayed or an alarm is given. Thus, it is possible to avoid a situation where irradiation of the measuring light is continued past the value of the MPE without being noticed by an operator.

(11) When the irradiation energy exceeds the predetermined value, the measuring light is controlled. Thus, it is unnecessary to conduct troublesome operations such as lowering a measuring light output or stopping the output of measuring light.

(12) When the irradiation energy exceeds the predetermined value, the control is conducted so as not to irradiate the measuring light to the eye to be examined. Thus, it is unnecessary for an operator to conduct troublesome operations such as lowering a measuring light output or stopping the output of measuring light based on the irradiation energy value.

As described above, in the ophthalmologic apparatus according to the present invention, the irradiation of the measuring light irradiation can be conducted in a manner such as not to exceed the MPE, while securing the safety at the same time.

What is claimed is:

1. An ophthalmologic apparatus comprising:
   an irradiation optical system for irradiating to an eye fundus region a light beam for examining the eye fundus region of an eye to be examined;
   selecting means for selecting an irradiating position of the light beam on the eye fundus region;
   a timer for measuring an irradiating time of the light beam; and
   control means for calculating integrated irradiation energy based on the irradiating time measured by the timer in accordance with the selected irradiating position on the eye fundus region of said eye to be examined,
   wherein the control means calculates an amount of integrated irradiation energy corresponding to the selected irradiating position on the eye fundus region for the each of the selected irradiating position.

2. An ophthalmologic apparatus according to claim 1, further comprising a sensor for monitoring output of the light beam, wherein the control means calculates the integrated irradiation energy for said each of the selected irradiating position based on an output of the sensor and the irradiating time measured by the timer.

3. An ophthalmologic apparatus according to claim 1, further comprising discriminating means for discriminating between left and right eyes to be examined, wherein the control means calculates the integrated irradiation energy for each of the left and right eyes based on a discrimination result from the discriminating means.

4. An ophthalmologic apparatus according to claim 1, wherein the control means calculates the integrated irradiation energy by assuming that a predetermined region corresponds to the same position as the selected irradiating position on the eye fundus region of the eye to be examined.

5. An ophthalmologic apparatus according to claim 1, further comprising a display means for displaying at least one of the integrated irradiation energy or a proportion of the integrated irradiation energy to a predetermined value, for an irradiation time at said each of the selected irradiating position.

6. An ophthalmologic apparatus according to claim 1, wherein, when a value of the integrated irradiation energy becomes a predetermined value or larger, an alarm is given or irradiation of the light beam is restricted.

7. An ophthalmologic apparatus according to claim 1, wherein the light beam is one of a measuring laser beam for measuring a blood flow rate in the eye fundus region and a tracking laser beam.

* * * * *

UNITED STATES PATENT AND TRADEMARK OFFICE
CERTIFICATE OF CORRECTION

PATENT NO. : 6,612,699 B2
DATED : September 2, 2003
INVENTOR(S) : Shigeaki Ono

It is certified that error appears in the above-identified patent and that said Letters Patent is hereby corrected as shown below:

<u>Column 10,</u>
Lines 48, 56 and 57, delete "light" and insert -- right --

Signed and Sealed this

Third Day of May, 2005

JON W. DUDAS
*Director of the United States Patent and Trademark Office*